United States Patent [19]

Pawliszyn

[11] Patent Number: 5,153,666
[45] Date of Patent: Oct. 6, 1992

[54] METHOD AND APPARATUS FOR DETECTING CONCENTRATION GRADIENTS

[75] Inventor: Janusz B. Pawliszyn, Waterloo, Canada

[73] Assignee: Anthony R. Torres, Salt Lake City, Utah

[21] Appl. No.: 657,066

[22] Filed: Feb. 19, 1991

Related U.S. Application Data

[63] Continuation-in-part of Ser. No. 271,008, Nov. 14, 1988, Pat. No. 4,993,832.

[51] Int. Cl.[5] .......................................... G01N 21/41
[52] U.S. Cl. ..................... 356/128; 356/129; 356/432
[58] Field of Search ................. 356/128–132, 356/344, 432, 362, 439, 440, 73.1

[56] References Cited

U.S. PATENT DOCUMENTS

| 2,780,955 | 2/1957 | Wiedemann . | |
|---|---|---|---|
| 3,623,361 | 11/1971 | Funk, Jr. . | |
| 4,468,136 | 8/1984 | Murphy et al. . | |
| 4,547,071 | 10/1985 | Teitelbaum . | |
| 4,673,810 | 6/1987 | Babsch et al. . | |
| 4,744,654 | 5/1988 | Jinno et al. | 356/128 |
| 4,784,494 | 11/1988 | Pawliszyn . | |
| 4,993,832 | 2/1991 | Pawliszyn | 356/128 |

OTHER PUBLICATIONS

Janusz Pawliszyn et al., Dual-Beam Deflection Sensor, Rev. Sci. Instrum. 56 (9), Sep. 1985.

Primary Examiner—Richard A. Rosenberger
Assistant Examiner—Hoa Pham
Attorney, Agent, or Firm—Mallinckrodt & Mallinckrodt

[57] ABSTRACT

The sensitivity of refractive gradient detectors for detecting refractive index gradients in samples flowing through samples chambers is increased by detecting the gradients formed in the direction perpendicular to the direction of flow of the sample through the sample chamber and by detecting such gradients simultaneously intermediate the central axis and sides of the sample chamber on opposite sides of the central axis. A preferred detector uses two spaced, parallel probe light beams passing through the sample chamber between the central axis and sides of the chamber on opposite sides of the axis, with each beam preferably centered about half way between the axis and the respective side. A sensor detects relative movement of the probe beams caused by a refractive index gradient in the sample but preferably compensates for parallel movement of the parallel light beams caused by positional instability or mechanical movement of the light source. The sensor produces an output signal proportional to the refractive index gradient detected.

18 Claims, 7 Drawing Sheets

METHOD AND APPARATUS FOR DETECTING CONCENTRATION GRADIENTS

RELATED APPLICATIONS

This is a continuation-in-part of my copending application Ser. No. 07/271,008, filed Nov. 14, 1988, entitled "Method and Apparatus for Detecting Concentration Gradients", now U.S. Pat. No. 4,993,832.

BACKGROUND OF THE INVENTION

1. Field

The invention is in the field of detection methods and apparatus based on Schlieren optics.

2. State of the Art

It has been known for some time that a refractive index gradient such as produced by a concentration gradient in a fluid such as a gas, liquid, or supercritical fluid, will cause deflection of light passed through the gradient. The optical method of observing and measuring the deflection of light caused by refractive index gradient fields is generally referred to as Schlieren optics. In the past, Schlieren images resulting from light deflections have been recorded on photographic plates and the plates then analyzed for light intensity distribution using densitometers. Recently, evaluation of the photographic images has been done by computer. These methods are useful in studying plasmas where very complicated toroidal and parabolic shapes are generated.

U.S. Pat. No. 4,547,071 discloses a sensor for measuring density gradients in a nonhomogeneous fluid sample using Schlieren optics. In such sensor, a laser light beam is directed through a sample chamber and is moved along said chamber. A quadrant light position sensor located on the opposite side of the chamber detects the deflection of the laser light beam as it is moved through the sample. The amount of deflection indicates the density gradient at any point in the sample. Rather than moving the laser beam along the sample chamber, the beam can be held constant and the sample moved within the chamber.

A current development in the field of high performance liquid chromatography (HPLC) is the open tubular capillary column which provides ultra high efficiency separation of sample components. This method can utilize very small sample volumes. Similarly, current capillary zone electrophoresis equipment can be used with extremely small volume samples. My U.S. Pat. No. 4,784,494, shows a detector that can be used to detect concentration and thermal gradients in very small samples. That detector utilizes a light source to generate a probe beam of light that is passed through the sample having the gradient to be detected or measured and the deflection of the probe beam is measured on a beam position detector. Various light sources may be used to generate the probe beam such as a laser or light emitting diode (LED).

With equipment that detects or measures concentration or other gradients present in a sample, the sensitivity of such equipment is limited by the extent of the gradient present in the sample. The concentration gradients associated with solutes eluting from typical HPLC columns are generally small due to significant band broading during the separation process with the result that sensitivity of the gradient detection using currently known detection equipment is poor. Thus, the single probe light beam detection equipment shown in my U.S. Pat. No. 4,784,494, or the dual probe light beam equipment shown in my parent application, when used in the embodiments specifically illustrated and described, are subject to poor sensitivity when the actual concentration gradients to be detected are small. Increased sensitivity in detecting small gradients would be desirable.

SUMMARY OF THE INVENTION

According to the invention, the sensitivity of detection of concentration gradients in samples flowing through a sample chamber is increased by passing light through the sample chamber and sample therein at positions intermediate the center of the chamber and the chamber sides through a portion of the sample having a slower flow rate than at the center of the chamber, and sensing the deflection of the light in a direction perpendicular to the direction of the flow of the sample. It has been found that with flow through the sample chamber, particularly with laminar flow conditions, the concentration gradients toward the sample chamber walls in the perpendicular direction are much greater than the gradient in the direction of flow. Thus, the sensitivity is much greater than with equipment measuring the deflection of the light beam in the direction of flow. Further, since similar gradients occur going from the center of the sample chamber toward the sides on all sides, if two parallel probe beams are used on opposite sides of the central axis of the sample chamber, the same sample gradient will cause opposite deflections for the beams the on opposite sides of the sample chamber, i.e., the beams will either be deflected toward the center of the chamber or away from the center of the chamber. With the proper detector, sensitivty is doubled by using two parallel beams.

In a preferred embodiment of the invention, a dector for detecting refractive index gradients within a sample flowing in a sample chamber includes a sensor having a sensing surface extending perpendicularly to the direction of flow of the sample in the sample chamber. Such direction will be referred to as the perpendicular direction. Light, from a source of light, is directed through the sample so that a portion of the light passing through the sample falls on the sensing surface of the sensor, a portion of the light falls off the sensing surface of the sensor on one side of the sensing surface toward one side of the sample chamber, and a portion of the light falls off of the sensing surface of the sensor on the opposite side of the sensing surface toward the opposite side of the sample chamber. With such an arrangement, deflection of the light caused by a refractive index gradient in the path of the light will produce either an increase or a decrease in the intensity of the light falling on the sensing surface and will produce an output of the sensor proportional to the relative movement of the light and proportional to the refractive index gradient causing the movement of the light. In addition, the portions of light falling off the opposite sides of the sensing surface are complementary portions so that movement of the light not caused by presence of a refractive index gradient in the path of the light, such as movement caused by vibration or positional instability of the light source, will move the respective complementary portions of the light equally in the same direction so that any increase in light falling off of the sensing surface at one side is equal to the increase in light falling onto the sensing surface at the other side to thereby maintain a constant output from the sensor.

The light passing through the sample and falling partially on and partially off the sensing surface of the sensor may be a pair of spaced light beams separated in the perpendicular direction or may be a single light beam.

A preferred detector of the invention which measures a refractive index gradient in a sample utilizes two spaced, parallel probe light beams passing through the sample with the beams separated along the perpendicular direction so as to pass through the sample intermediate the center of the sample chamber and opposite sides of the chamber. A sensor measures the differential movement of the two beams. In order to compensate for positional instability of the light beams, the two probe beams are preferably generated by the same light source, such as the same laser, and then split into the parallel separate beams. When the beams are passing through a sample without a gradient present, the sensor senses only complementing portions of each beam so that if the beams move in parallel, as would be the case during beam positional shifts of a source laser, the output of the sensor remains the same. If relative movement in the perpendicular direction occurs between the two beams as will occur as a refractive index gradient is encountered by each beam, an output is produced by the sensor proportional to the relative beam movement.

The sensor preferably includes a single photodiode initially calibrated so that one half of each of the beams fall on the photodiode at a sharp edge of the sensing surface. This can be accomplished by providing a mask over the photodiode to provide a sharp edge for the sensing surface and positioned so that the probe beams are divided in half with the halves toward each other falling on the sensing surface. The division of the beams will be along lines parallel to the direction of flow of the sample to be measured. In this way, when one beam moves in the perpendicular direction with respect to the other beam, i.e., the beams move toward one another toward the center of the sample chamber or away from one another away from the center of the sample chamber, either more of the beams or less of the beams fall on the sensing surface so the output of the sensor is either increased or decreased, respectively. However, any parallel movement of the probe beams in the perpendicular direction will cause less of one beam to fall on the sensing surface but an equal amount more of the other beam to fall on the surface so that the overall light falling on the surface is the same. When the parallel probe beams are created by splitting a single laser beam into two beams, the positional instability of the laser will create parallel movements of the parallel beams. Since parallel movements of the probe beams are canceled out by the sensor, the sensor output has been compensated for the laser positional instability.

By using two beams which are both simultaneously deflected toward the center of the chamber or away from the center of the chamber by any gradient passing through the chamber, the sensitivity of detection and measurement of the gradient is doubled. This increase in sensitivity is in addition to the increase in sensitivity obtained by measuring deflection in the perpendicular direction rather then in the direction of sample flow as done in prior art detection.

THE DRAWINGS

The best mode presently contemplated for carrying out the invention is shown in the accompanying drawings in which.

DETAILED DESCRIPTION OF THE PREFERRED EMBODIMENT

Figure 1:
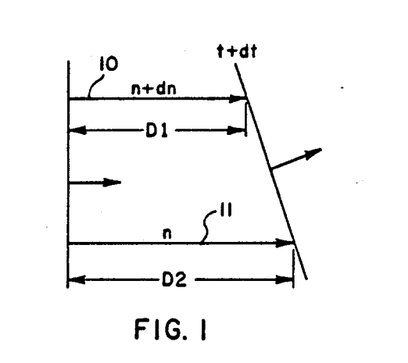
FIG. 1 is schematic representation of a light beam passing through a gradient.

It is well known that light passing through a refractive index gradient in a solution is deflected. The physical reason for light deflection when passing through this gradient lies in the relationship between the refractive index and light propagation velocity. Different parts of the light advance to a different degree with time, which generates the phase shift. Thus, as shown in FIG. 1, during a given time period t+dt, light at the top of a light beam indicated by arrow 10 which is passing through a solution with a refractive index of n+dn will travel a distance of D1. The light at the bottom of the light beam indicated by arrow 11 which is passing through a solution with a refractive index of n will travel a distance D2. This results in a tilt of the light wavefront and since light travels perpendicular to the wavefront, the light beam is tilted as illustrated. In FIG. 1, D2 is greater than D1 resulting in an upward tilt, but depending upon the values of n and n+dn, the tilt could be downward.

The light path through the refractive index gradient can be calculated by using the Fermat principle that the light path through the medium is such that the time necessary for its traversal is minimum. The relationship between the angle of deflection, $\theta$, and the refractive index gradient normal to the light propagation dn/dx and path length through this gradient, D, can be written as $$\tan \theta = \sin h$$
$$(D/n)(dn/dx) = (D/n)(dn/dx) + (dn/dx)^3(D^3/n^3 3!) + (dn/dx)^5(D^5/n^5 5!) + \ldots$$

where n is the refractive index of the medium. In situations where the sensor of the invention will be used, D and $\theta$ are small. We can then approximate:

$$\theta = (D/n)(dn/dx)$$

Figure 2:
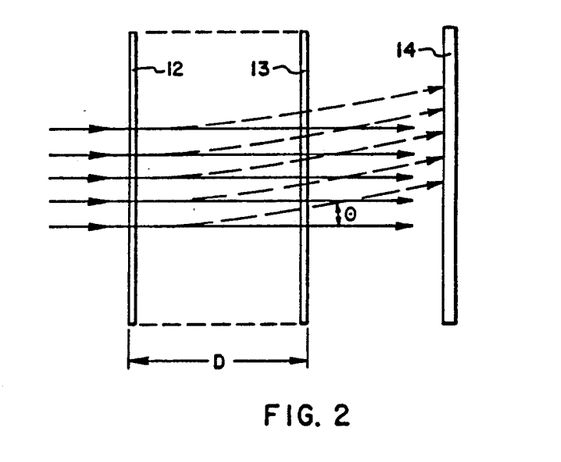
FIG. 2, a schematic representation of a light beam passing through a sample chamber, showing the deflection angle produced by the presence of a refractive index gradient in the chamber.

FIG. 2 illustrates the detection principle behind this method. With a nonuniform distribution of a solute in the sample chamber shown schematically between sample chamber walls 12 and 13 giving a sample chamber distance D, a concentration gradient is established. This gradient forms the corresponding refractive index gradient $dn/dx = (dn/dc)(dc/dx)$, which then tilts or deflects the propagating light beam by angle $\theta = (D/n)(dn/dc)(dc/dx)$. This deflection can be measured by measuring the position of the light beam on the position detector 14. The information produced during the measurement of the concentration gradient relates to the universal property of the solute — refractive index n. Consequently, the concentration gradient produced by any solute that has a different n than the solvent will be detected by noting a deflection or tilt in the light beam.

Figure 3:
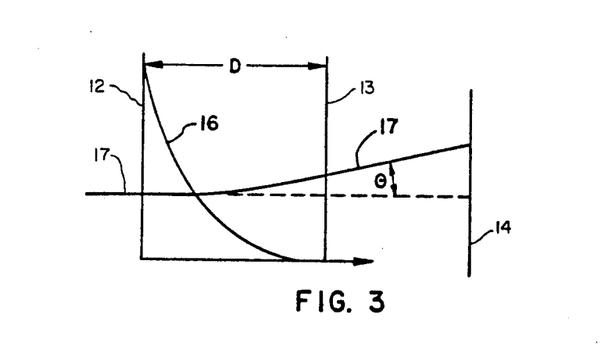
FIG. 3, a second schematic representation of a light beam passing through a sample chamber with a concentration gradient.

FIG. 3 shows the same principal as FIG. 2, but illustrates it somewhat differently. Thus, if a concentration gradient represented by line 16 exists in a sample in a sample chamber defined by walls 12 and 13, a probe beam of light 17 directed through the sample will be deflected as indicated above by an angle $\theta$. This causes the position of the beam to move on the surface of the position sensor 14 as indicated above.

When a sample flows through a sample chamber, the velocity of the sample close to the chamber wall is lower than the velocity in the center of the chamber. Therefore, the composition of the sample, i.e., the mobile phase with solute therein, is highly inhomogeneous as it flows through the sample chamber.

Figure 4:
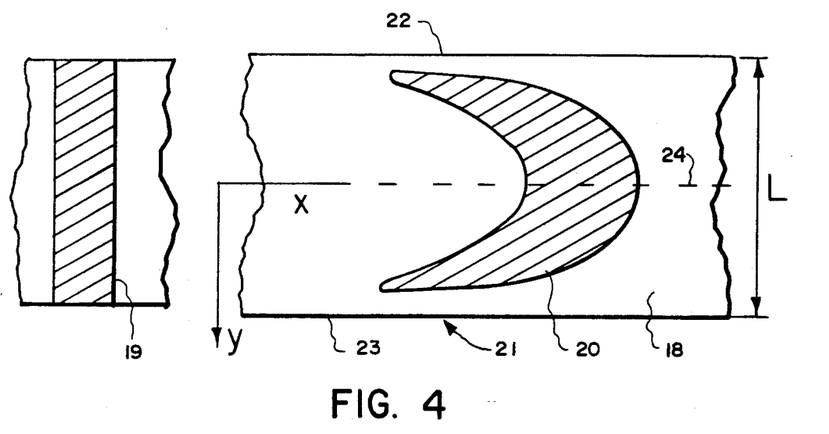
FIG. 4, a schematic representation of a sample flowing through a sample chamber.

FIG. 4 illustrates this situation wherein a sample including a mobile phase 18 with solute plugs 19 and 20 therein is flowing through a sample chamber 21. With sample flow through the sample chamber, flow adjacent the chamber walls 22 and 23 is slower than flow in the center of the chamber along central chamber axis 24. When the flow is laminar, the flow results in the spreading of the solute plug 19 as the sample flows so that a plug 19 as it emerges from a chromatography column or is injected into a mobile phase 18 to flow through the sample chamber takes the form of plug 20 after flowing a certain distance.

In general, the concentration profile C(x,r) of a solute plug expressed as a function of the position in the direction of flow, referred to as the axial (x) position, and the position in the direction perpendicular to the direction of flow, referred to as the perpendicular (y) direction or radial (r) direction, as generated by laminar flow in a tube, can be described by the equation:

$$C(r,x) = C(r = 0,x) + \frac{u}{4D_M}\left(r^2 - \frac{r^4}{2R^2}\right)\frac{dC(r = 0,x)}{dx}$$

where $C(r=0;x)$ and $dC/dx(r=0,x)$ are the concentration and its gradient, respectively, in the center of the tube expressed as a function of the axial position x; R is the diameter of the tube, $D_M$ is the diffusion coefficient of the solute in the mobile phase, and u is its linear velocity. The parabolic concentration profile of a solute plug such as 20, FIG. 4, will produce a symmetric "concentration lens" in the sample chamber. The optical inhomogeneities associated with the concentration profiles can be used effectively in gradient detection, for example, by probing the curvature of the parabolic lens. Using a square sample chamber, as is presently preferred for the dector of the invention, the gradients of concentration in the perpendicular (y) direction which define the curvature of the refractive index in the sample chamber, can be calculated as a derivative of C(x,y) from the above equation where, for the square sample chamber, the radial position r is replaced with the perpendicular dimension y:

$$\frac{\partial C(y,x)}{\partial y} = \frac{u}{2D_M}\left(y - \frac{4y^3}{L^2}\right)\frac{\partial C(y = 0,x)}{\partial x}$$

The maximum of the curvature can be derived from the condition:

$$\frac{\partial^2 C(y,x)}{\partial y^2} = 0$$

which is reached for $y = L/(2\sqrt{3})$ (about half way between the center and the chamber wall), where L = the distance between opposite chamber walls 22 and 23. At this position, the gradient in the perpendicular direction is at the maximum and at all times can be related to the concentration gradient produced at the center of the flow in the vertical direction:

$$\frac{\left(\frac{\partial C}{\partial y}\right)_{max}}{\left(\frac{\partial C}{\partial x}\right)_{y = 0}} = 0.193 \frac{uR}{D_M}$$

For typical experimental arrangements, this ratio is about 2000 ($D_M = 10^{-5}$ cm$^2$/s; u = 1 cm/s, L = 1 mm), which clearly indicates that under the laminar flow conditions the concentration gradients are much higher in the horizontal than in the axial direction. This, in turn, will enhance the sensitivity of concentration gradient detection by several orders of magnitude. In practice the total increase in the gradient magnitude measured is composed of two factors, one associated with the parabolic flow profile discussed above and the other with the expansion of the solute in the mobile phase. To obtain the highest sensitivity in this detection scheme, the volume of the cell should be optimized carefully. A sample chamber that is very small compared to the peak volume will limit the sensitivity, while a large sample chamber will reduce the resolution.

Figure 5:
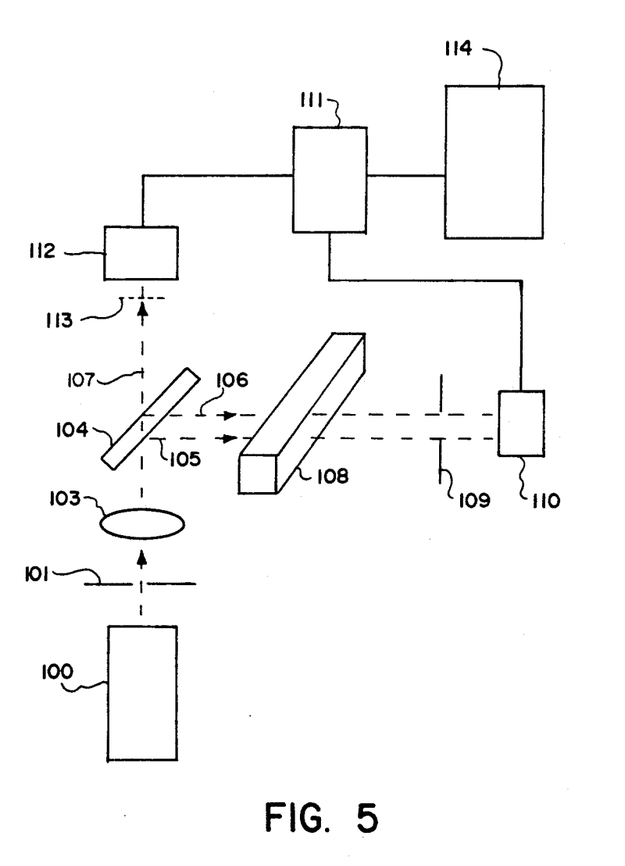
FIG. 5, a block diagram of a detector of the invention.

The symmetry of the parabolic flow can be used to enhance detection and sensitivity by using a dual probe beam detector. FIG. 5 shows a block representation of an embodiment of a dual beam detector system of the invention. The detector includes a light source 100, such as a Helium-Neon laser. The light from light source 100 passes through an iris 101 to a lens 103 and beam splitter 104, which produces the two probe beams 105 and 106, and an optional reference beam 107. The beam splitter 104 merely reflects one beam from the front surface and one beam from the rear surface of the splitter, while the reference beam passes through the splitter. The two probe beams are directed through sample chamber 108 and pass through an adjustable aperture 109 to a sensor 110. The two probe beams are spaced in the perpendicular direction by a distance centered at the center of the sample chamber so that the probe beams pass through the area of the sample having the highest gradient generated in the perpendicular direction. The "parabolic lens" generated by flow through the sample chamber will cause deflection of both beams either toward the center of the chamber, i.e., toward one another, or away from the center of the sample chamber, i.e., away from one another, depending on the orientation of the refractive index gradient in the sample. Thus, when deflected by a refractive index gradient, either more or less of the beams fall on the sensor. The output of the sensor 110 is connected to a differential amplifier 111, which is also connected to the output of reference detector 112. The reference light beam 107 passes through a neutral density filter 113 and falls on reference detector 112 to provide an output reference signal to differential amplifier 111. The output of differential amplifier 111 is sent to computer 114 for evaluation, storage, and output.

Figure 6:
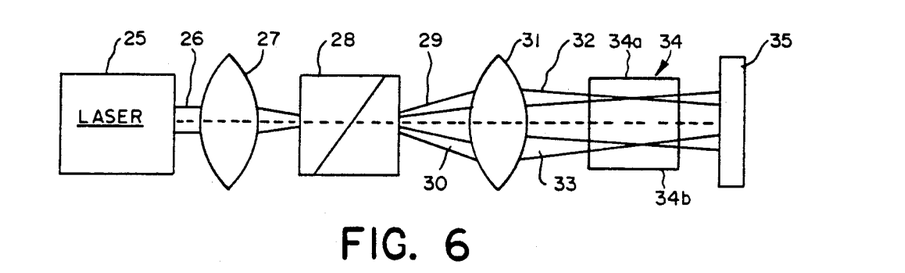
FIG. 6, a schematic representation of a detector of the invention.

A basic dual beam detector of the invention is shown schematically in FIG. 6. The detection apparatus includes a laser 25, which generates a laser beam 26 directed to a lens 27 which focuses the beam into a Wollaston prism 28. The Wollaston prism 28 splits the beam 26 into two beams 29 and 30. A lens 31 is positioned in the path of the two beams 29 and 30 so as to focus the beams as two parallel beams 32 and 33 passing through a sample chamber 34. The distance between the parallel beams is adjusted by adjusting the distance between Wollaston prism 28 and lens 31. The sample chamber 34 is located at the focal point of the parallel probe beams. After passing through the sample chamber, the parallel probe beams 32 and 33 fall on a sensor 35 which measures the relative movement of one probe beam with respect to the other, i.e., measures the differences in movement of the two beams. As indicated above, the probe beams are located in a plane perpendicular to the direction of flow of the sample and are positioned so that their focal points are located approximately half way between the center of the sample chamber indicated by the dotted line, and opposite sides 34a and 34b of the sample chamber 34. Flow through the sample chamber may be either out of the page or into the page. The sensor 35 is arranged to measure probe beam deflection in the perpendicular direction, i.e., toward or away from the center of the sample chamber, and this measures refractive index gradients which exist in the perpendicular direction in the sample.

Figure 7:
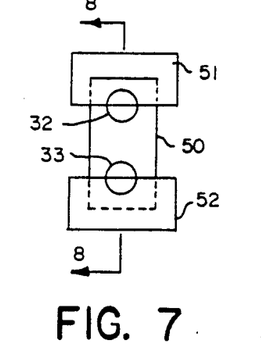
FIG. 7, a front view of the light beam sensor of FIG. 6.
Figure 8:
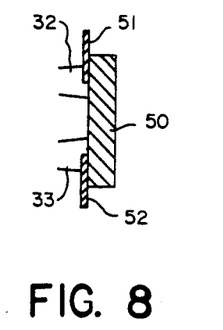
FIG. 8, a vertical section through the sensor of FIG. 7 taken on the line 8—8 of FIG. 7.
Figure 9:
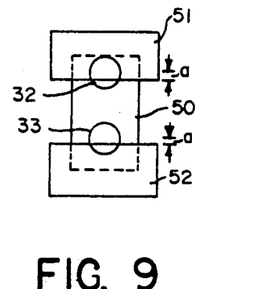
FIG. 9, a front view of the light beam sensor of FIG. 7 similar to that of FIG. 7, but showing the light beams in a different position.

While various types of sensors could be used to measure the deflection of the probe beams in the perpendicular direction, it has been found that a sensor constructed to measure only complementary portions of each probe beam when no refractive index gradient is present in the sample provides various benefits. With such a sensor, parallel movement of the beams, such as might result from vibrational movement of the laser or from movement of the laser beam resulting from the inherent positional instability of the laser beam, will change substantially equally the respective complementing portions of the beams sensed to maintain a constant output from the sensor. However, movement of one beam with respect to the other beam, as when the beams are each deflected by a concentration gradient, will provide an output of the sensor proportional to the relative movement of the beams. In the particular embodiment shown, the sensor is constructed with a single photosensor 50, FIGS. 7-10, such as a single photodiode. An S1087-01 from Hammamatsu of Middlesex, N.J. has been found satisfactory. The upper and lower ends of the photosensor 50 are covered or masked by upper and lower end covers 51 and 52, respectively, (the adjustable aperture 109 of FIG. 5) which are preferably position adjustable with respect to photosensor 50. The sensor 35 is positioned with respect to upper and lower probe light beams 32 and 33 such that for each beam, one half of the beam falls on the photosensor and one half of the beam falls on an end cover. Thus, as shown in FIGS. 7 and 8, the photosensor 50 and the end covers 51 and 52 are positioned so that with no refractive index gradient present in the sample chamber so that probe beams 32 and 33 pass directly through the chamber without being deflected, the lower half of upper beam 32 falls on photosensor 50 and the upper half of upper beam 32 falls on cover 51 and is thereby blocked from falling on photosensor 50. The upper half of lower beam 33 falls on photosensor 50 and the lower half of lower beam 33 falls on cover 52 and is blocked from photosensor 50. Thus, only one-half of each beam falls on the photodetector. With this arrangement, if the probe beams move in parallel, such as would occur due to the positional instability of a laser light source for the probe beams or would occur due to vibration of the laser, the output of the sensor remains the same and such movement and instability is compensated for. For example, if the probe beams both move upwardly a distance "a" as shown in FIG. 9, more of beam 32 falls onto cover 51 and less onto photosensor 50. However, now less of beam 33 falls onto cover 52 and more falls onto photosensor 50. The portion of beam 32 moving onto cover 51 equals the portion of beam 33 moving onto photosensor 50 so the net result due to the parallel movement of the beams is that the same amount of light falls onto the photosensor before and after the parallel movement of the beams so the sensor sees no change and no change in sensor output occurs. The arrangement of the sensor and beams is such that complementary portions of each beam, i.e., in the embodiment shown, the lower half of upper beam 32 and the upper half of lower beam 33, fall onto the photosensor while complementary portions of each beam, i.e., the upper half of beam 32 and the lower half of beam 33, fall onto the respective covers. With circular light beams, as shown, or other beams having a light intensity distribution across the beams in the direction of the expected gradient, the complementary portions of the beams will usually be such that when added together they equal one beam. Rectangular beams having equal light intensity distribution over the beam in the direction of the expected gradient may have complementary portions which add up to less than, equal to, or greater than a single beam, as long as the complementary portions add up to the same total value throughout the entire expected range of movement of the beams to be compensated for.

Figure 10:
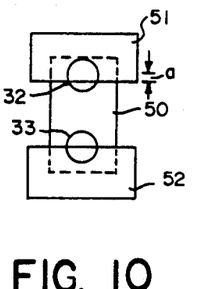
FIG. 10, another similar front view of the sensor showing the light beams in a still different position.

If relative movement of the probe beams take place, such as if upper beam 32 moves upwardly a distance "a", FIG. 10, due to a refractive index gradient in the sample chamber in front of beam 32, but beam 33 does not move because no refractive index gradient has yet reached a position in front of it in the sample chamber, less light from beam 32 falls on the photosensor 50 from beam 32, and only the same amount falls on photosensor 50 from beam 33 so the total light falling on photosensor 50 is reduced and its output will be reduced. In the situation described above with detection in the perpendicular direction, rather than only one beam moving, both beams would move simultaneously the distance "a" in opposite directions, i.e., beam 32 upwardly and beam 33 downwardly, so both would move in a manner to lessen the light falling on photosensor 50. Thus, the change in output of photosensor 50 is twice as much for a gradient where both beams move as where only a single beam moves. It will be seen that relative movement of the two beams 32 and 33 with respect to each other, as will be caused by a refractive index gradient moving through the sample chamber, will cause either more light, if the beams move toward one another, or less light, if the beams move away from one another, to fall onto photosensor 50 than when no relative movement takes place, and such relative movement of the two probe beams with respect to each other will cause a change in the output from the sensor. The output of the sensor will be proportional to the differences in movement between the two beams.

While the sensor of FIGS. 7-10 shows a photosensor 50 and end covers 51 and 52, the end covers merely provide sharp, defined edges for the photosensor. Thus, a photosensor without the covers could be arranged so that the light beams merely overlap the edges of the photosensor. In such instance, the positions of the two light beams may be adjusted by adjusting the distance between the Wollaston prism 28 and lens 31 so that the beams are properly positioned to fall on the edges of the photosensor. However, if the beams are moved substantially from their positions at the location of maximum gradient, sensitivity will be reduced by such movement. The end covers are presently preferred because it makes it easier to properly adjust the amount of each beam falling on the photosensor. Razor blades have been found to work well as end covers.

Figure 11:
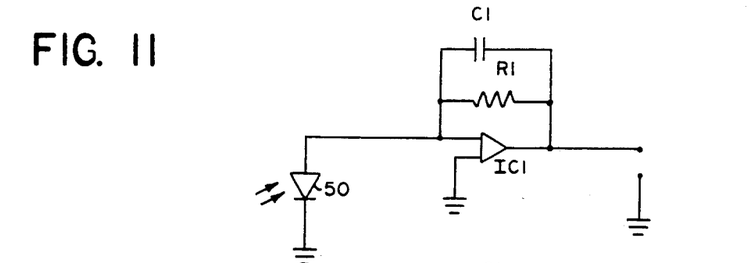
FIG. 11, a circuit diagram of circuitry usable with the invention.

The output of the photosensor 50 is a curve representative of the differences in movement between the two probe beams, and is proportional to the refractive index gradient passing through the beams. Usually the output will be amplified prior to being fed to a chart recorder, computer, or other equipment which will utilize the signal and a simple amplifier circuit as shown in FIG. 11 may be used. The photosensor 50, such as the photodiode indicated above, is connected to one input of an operational amplifier IC1 such as an OPA-111 manufactured by Burr Brown of Tuscon, Ariz. The gain of the amplifier is set in normal fashion by feedback resistor R1 and the bandwidth of the amplifier is set by capacitor C1. The circuitry is set to operate in the substantially linear range of the photodiode 50 and the light normally falling on it is not sufficient to saturate it. Thus, as the light falling on the photodiode varies, the current flowing through it, and thus the voltage across it, varies. The varying voltage is amplified by IC1 and provides the output.

Figure 12:
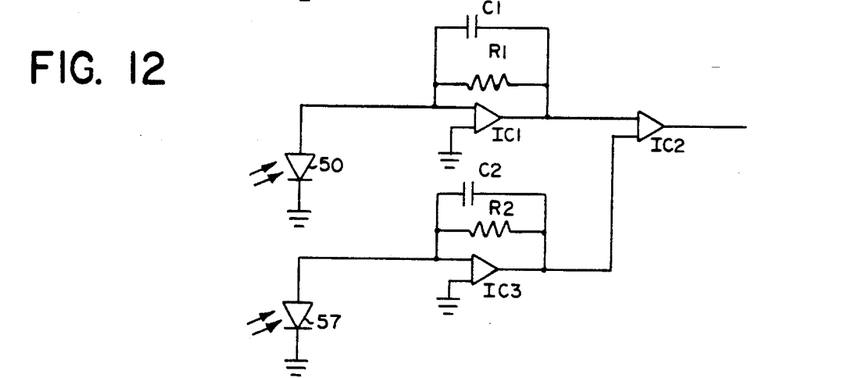
FIG. 12, a circuit diagram of a different embodiment of circuitry usable with the invention.

If it is desired to compensate the output of the photosensor for any intensity variations in the light beam intensity, as done in the system shown in FIG. 5, a compensation circuit such as shown in FIG. 12, can be used. In such instance, the laser beam 26 from laser 25 may be split as by placing a glass side 55, FIG. 13, in such beam to deflect a portion of the beam as a reference beam 56 to a photosensor 57, (corresponding to reference beam 107 and reference detector 113 in FIG. 5) such as a photodiode similar to that used for sensor 50.

The circuit of FIG. 12 contains the circuitry of FIG. 11 with the output of IC1 connected to an input of differential amplifier IC2 which may be OPA101 manufactured by Burr Brown. This corresponds to differential amplifier 111 of FIG. 5. The output of photosensor 57, which varies if the intensity of the laser beam generating the probe beam varies is amplified similarly to the output of photodiode 50 with IC3, R2 and C2 operating similarly to the amplifier previously described. The output of IC2 is a signal representative of the output of photodiode 50, but compensated for any change in light intensity of the probe beam.

Figure 13:
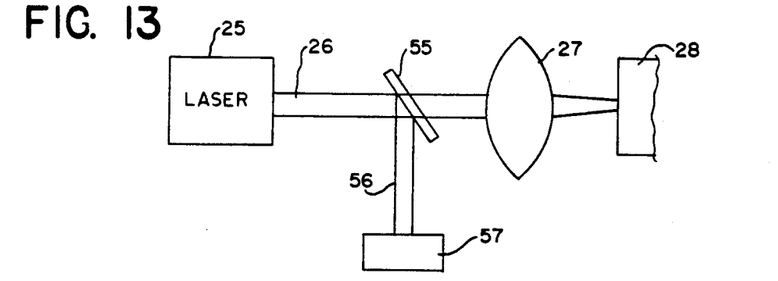
FIG. 13, a fragmentary schematic representation of the detector of FIG. 6, showing a modification to a portion thereof.
Figure 14:
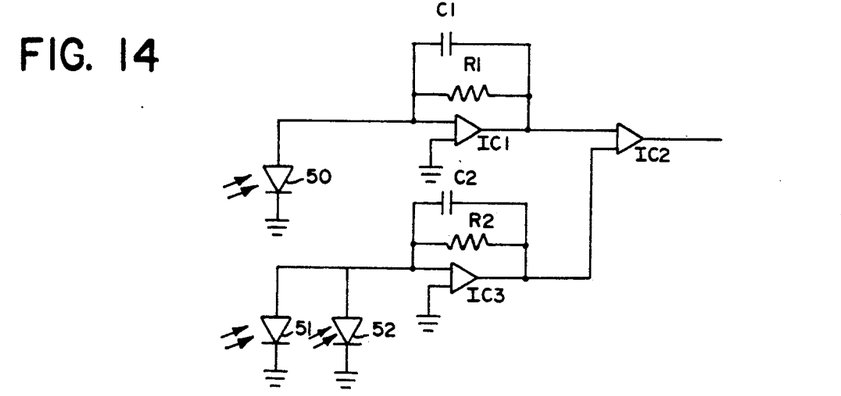
FIG. 14, a circuit diagram similar to that of FIG. 12, but showing two reference photodiodes.

Rather than generating a separate reference beam 56 as shown in FIG. 13, the end covers 51 and 52 for photosensor 50 could themselves be additional photosensors, such as photodiodes. In such case, the photodiode end covers could be substituted directly in the circuitry of FIG. 12 for photodiode 57, as shown in FIG. 14, and serve to compensate the output of photodiode 50 for any light intensity fluctuations.

Figure 15:
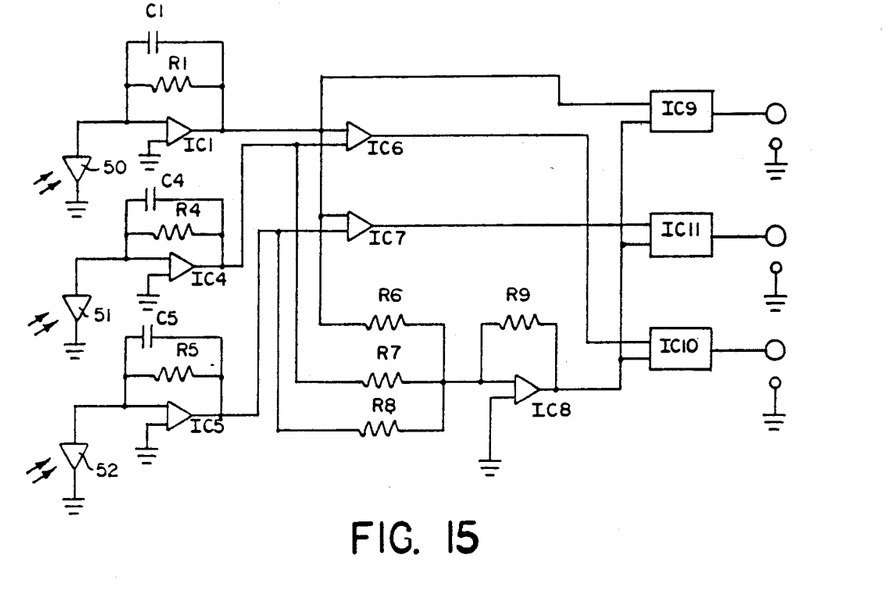
FIG. 15, a circuit diagram of still different circuitry usable with the invention.

If end covers 51 and 52 are themselves photosensors, each of the covers, in combination with photosensor 50, can form an individual position detector for an individual probe beam, if desired. Circuitry showing individual beam positions as well as the difference in movement of the beams is shown in FIG. 15. Each of the three photodiodes 50, 51, and 52 have their own amplifier circuitry similar to the circuitry of FIG. 11. Thus, photodiode 50 has amplifier circuitry labeled identically to FIG. 11. The amplifier for upper photodiode 51 is made up of operational amplifier IC4, resistor R4 and capacitor C4. The amplifier for lower photodiode 52 is made up of operational amplifier IC5, resistor R5, and capacitor C5. The outputs of IC1 and IC4 are inputs to differential amplifier IC6 which measures the difference or change in light falling on photodiodes 50 and 51, respectively. The outputs of IC1 and IC5 are inputs to differential amplifier IC7 which measures the difference or change in light falling on photodiodes 50 and 52, respectively. The outputs of IC1, IC4, and IC5, which represent the total light falling on all three photodiodes, and thus the total illumination of the photodiodes provided by the probe beams, are passed through summing resistors R6, R7, and R8 to the input of operational amplifier IC8 which acts as a summing amplifier. Gain is determined by resistor R9. In order to provide the signal from photodiode 50 representative of the refractive index gradients, and compensated for illumination intensity variations, the output of IC1 is connected to an input of a divider IC9 such as a DIV 100 made by Burr Brown. The output of IC8, the signal representative of total illumination intensity, is also connected as an input to IC9. The output of IC9 is the desired signal compensated for intensity fluctuations. The output of IC6 is connected as an input along with the output of IC8 to divider IC10 to produce a signal proportional to the position of upper beam 32 compensated for light intensity fluctuations. Similarly, the output of IC7 is connected as an input along with the output of IC8 to divider IC11 to produce a signal proportional to the position of lower beam 33 compensated for light intensity fluctuations. These position signals may be used as desired.

Figure 16:
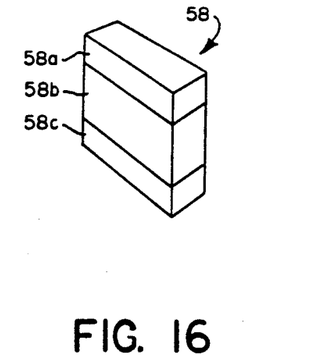
FIG. 16, a perspective view of a different embodiment of sensor.

Rather than using a photodiode 50 with separate end covers 51 and 52 which are also photodiodes, a triple photodiode 58, FIG. 16, may be fabricated having individual photodiodes 58a, 58b, and 58c built together as a single unit. Such a sensor would be used as described for the sensor of FIGS. 7-10 with the photodiodes 58a, 58b, and 58c replacing photodiodes 51, 50, and 52, respectively, in the various circuits described.

Figure 17:
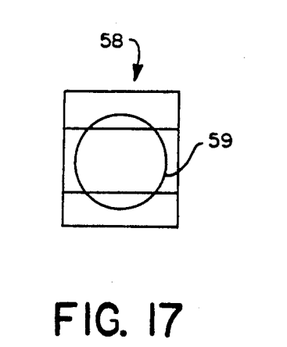
FIG. 17, a front view of a sensor of FIG. 16, showing a single light beam falling thereon.

As mentioned earlier, rather than using two separate light beams, a single beam can be used. FIG. 17 shows the sensor 58 of FIG. 16 with a single beam 59 thereon. The single beam is projected through the sample chamber to fall on the sensor as shown. Parallel movement of the beam will be compensated for while movement of portions of the beam to change the intensity distribution in the beam will be detected similarly to differential or respective movement of the two beams, as described. The same detector circuitry can be used. It is presently preferred to use two beams rather than a single beam because with two beams the higher intensity centers of the beams are directed on the edges of the sensing surface of the sensors which results in increased sensitivity with the two beams as opposed to the single, larger beam.

Experimental measurement of inaccuracies due to laser positional drift indicates two orders of magnitude reduction for the specific sensor described above for use with the system of the present invention compared to a single laser beam system, such as shown in my referenced U.S. Pat. No. 4,784,494.

The lower detection limits for gradient values obtained using the dual beam detector of the present invention arranged to measure deflection in the perpendicular direction are over an order of magnitude lower compared to conventional refractive index detectors. In addition, the cell volume is about 0.1 uL and can be made several orders of magnitude smaller, which makes this detector not only applicable to conventional HPLC but also to micro scale liquid chromatography.

Figure 18:
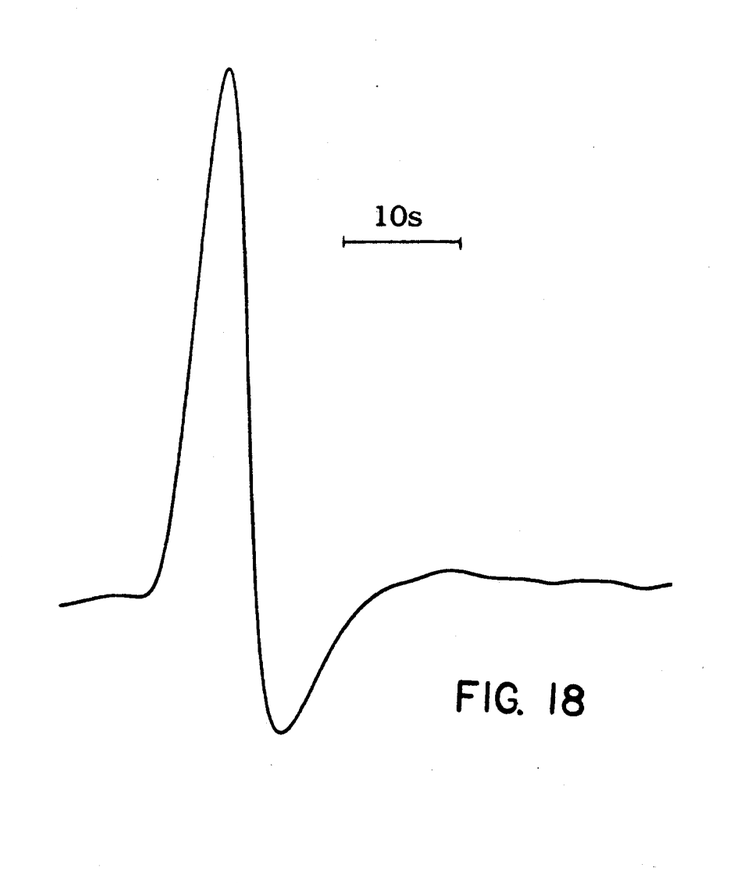
FIG. 18, a curve representing the concentration profile of a sample sent through a detector of the invention and produced as the output signal by the detector.

FIG. 18 shows a signal produced using the dual beam detector of the invention as shown in FIG. 5 with a sample obtained by eluting a peak consisting of a few picomoles of polyacrylic acid MW=250,000. The sample chamber was square with inside side dimensions of 2 mm and the flow rate through the chamber was 0.03 milliliters per minute. Water was the mobile phase. This clearly illustrates the high sensitivity of the gradient detector towards high molecular weight compounds due to the large dn/dC of such compounds.

Figure 19:
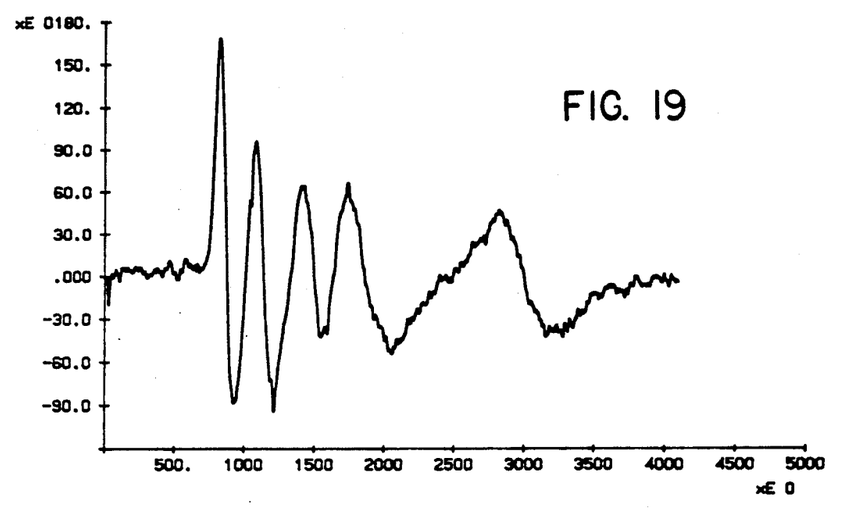
FIG. 19, another curve representing the concentration profile of a sample sent through a detector of the invention and produced as the output signal by the detector.
Figure 20:
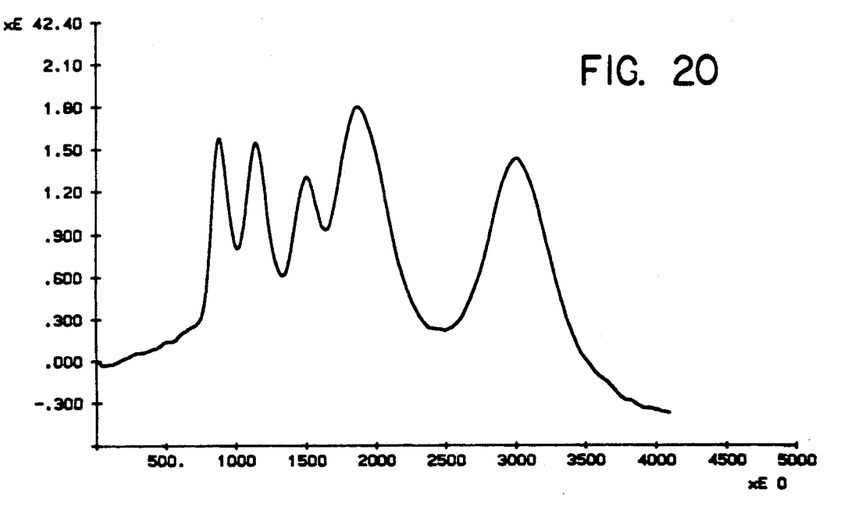
FIG. 20, a curve representing the integral of FIG. 19.

FIG. 19 shows a signal produced by separating sugars on a C18 bonded column (300×1 MM ID), and eluting the column to produce peaks of $3\mu$ grams each of glucose, sucrose, and raffinose, a $7.5\mu$ gram peak of maltopentaose, and a $7.6\mu$ peak of maltoheptaose. The sample column was 2 mm ID square and the flow rate through the sample column was 0.03 millileters per minute. Water was the mobile phase. FIG. 20 shows the integral of the curve of FIG. 19 which represents the actual concentration detected.

Figure 21:
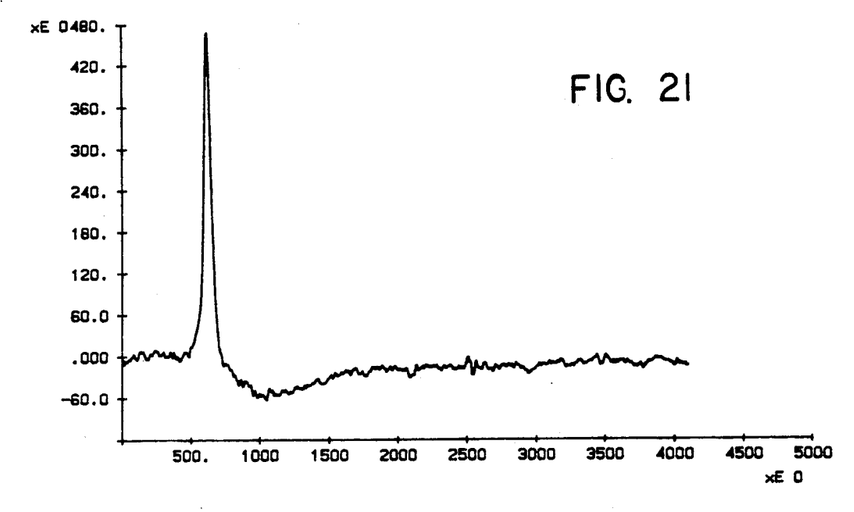
FIG. 21, another curve representing the concentration profile of a sample sent through a detector of the invention and produced as the output signal by the detector.
Figure 22:
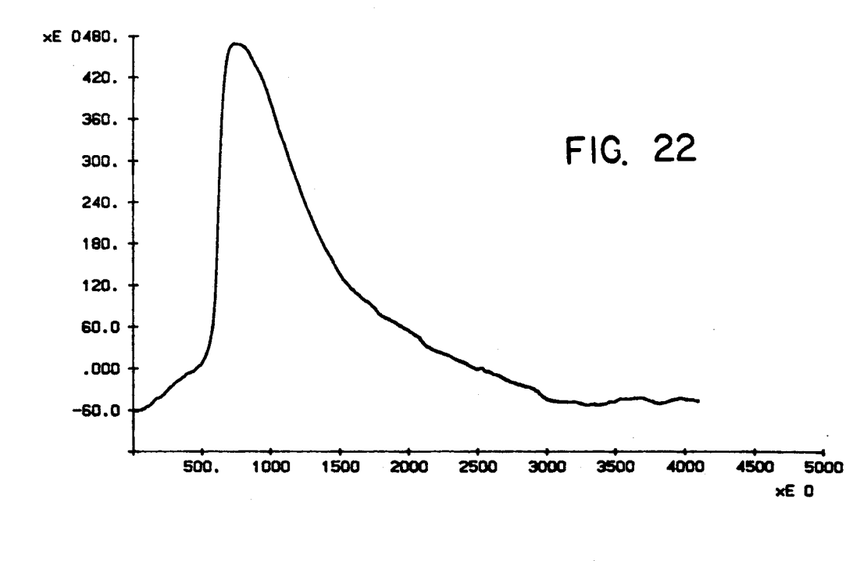
FIG. 22, a curve representing the integral of FIG. 21.

FIG. 21 shows a signal produced by a sample of 0.31% polyacrylic acid injected into water flowing through the sample chamber at the linear rate of 1 mm/sec. The sample chamber is the same as used above. FIG. 22 shows the integral of FIG. 21 which again represents concentration detected.

The invention also includes the method of detecting refractive index gradients by using two probe beams and a detector that detects beam movement in the perpendicular direction for sample flowing through a sample chamber.

Whereas this invention is here illustrated and described with specific reference to an embodiment thereof presently contemplated as the best mode of carrying out such invention in actual practice, it is to be understood that various changes may be made in adapting the invention to different embodiments without departing from the broader inventive concepts disclosed herein and comprehended by the claims that follow.

I claim:

1. A detector for detecting refractive index gradients within a sample flowing through a sample chamber, comprising an elongate sample chamber having side walls defining the chamber and having a central axis and through which a sample flow; means for generating two spaced, parallel probe light beams; means for passing the light beams through the sample chamber so that the light beams pass through the sample chamber intermediate the central axis and side walls of the chamber, each beam passing through the chamber on an opposite side of the central axis; and sensor means to detect deflection of the light beams in a direction perpendicular to the direction of flow of a sample through the sample chamber, deflection of said light beams being proportional to the refractive index gradients existing in the sample in a direction perpendicular to sample flow.

2. A detector according to claim 1, wherein each probe beam passes through the sample chamber centered approximately half way between a side wall and the central axis.

3. A detector according to claim 2, wherein the sensor means is a single sensor located in the path of both beams after passing through the sample chamber and adapted to measure only complementary portions of each beam when no refractive index gradient is present in the sample so that parallel movement of the beams will change equally the respective complementary portions sensed to maintain a constant output from the sensor, but movement of one beam relative to the other will produce an output proportional to the relative movement.

4. A detector according to claim 3, wherein the sensor is a photosensor having a sensing surface, and wherein the photosensor is arranged with respect to each of the probe beams so that only the complementary portions of each beam to be measured fall onto the sensing surface of the photosensor.

5. A detector according to claim 4, wherein the sensing surface of the photosensor is defined by a mask covering a portion of the sensing surface to prevent any portion of a beam falling on the mask from falling on the sensing surface of the photosensor.

6. A detector according to claim 5, wherein a mask is located along each of two opposite sides of the photosensor to provide two opposite, sharply defined edges of the sensing surface along said two opposite sides, wherein the opposite edges are parallel to the direction of flow of the sample through the sample chamber, and wherein respective probe beams and the photosensor are arranged so that each probe beam falls partially on the sensing surface of the photosensor and partially on a mask.

7. A detector according to claim 6, wherein the respective probe beams and the photosensor are arranged so that with no refractive index gradient in the path of the respective probe beams, the sum of the complementary portions of the respective probe beams falling on the sensing surface of the photosensor will remain the same through an expected range of parallel movements of the probe beams with respect to the photosensor.

8. A detector according to claim 7, wherein the sum of the complementary portions of the respective probe beams falling on the sensing surface of the photosensor when no refractive index gradient is in the path of the respective beams is equal to a single one of the probe beams falling completely on the sensing surface of the photosensor.

9. A detector according to claim 8, wherein the sensing surface of the photosensor is variably defined so as to adjust the sensing surface so that only the complementary portions of each beam to be measured fall onto the sensing surface of the photosensor.

10. A detector according to claim 9, wherein the photosensor is a photodiode.

11. A detector according to claim 6, wherein the masks are also photosensors which sense the portions of the probe beams falling on the masks.

12. A detector according to claim 1, wherein the probe light beams are generated by a laser.

13. A detector according to claim 12, wherein the two probe beams are generated from a single laser beam by splitting the single laser beam into the two beams.

14. A detector according to claim 1, wherein the refractive index gradient to be measured is caused by a concentration gradient of a component within the sample, wherein the flow through the sample chamber is substantially laminar; wherein the distance between opposite side walls of the chamber is equal to L; and wherein the probe beams are centered on opposite sides of the central axis at a position approximately defined by $L/2\sqrt{3}$.

15. A detector according to claim 1, wherein the sample chamber is configured to produce laminar flow of the sample through the sample chamber.

16. A method of detecting, with improved sensitivity, refractive index gradients within a sample, and producing an output signal approximately representative of the refractive index gradient, comprising the steps of flowing a sample having a refractive index gradient therein through a sample chamber having opposite sides forming the chamber and a central axis, so that flow of the sample is slower along the walls than in the center of the chamber to create a refractive index gradient in the sample in a direction perpendicular to the direction of sample flow; passing two spaced, parallel light beams through the sample having a refractive index gradient to be detected, each of the light beams passing through the sample intermediate the central axis of the sample chamber and the sample chambers sides and on opposite sides of the central axis; measuring the relative deflections of the light beams in the direction perpendicular to the direction of flow through the sample chamber as they pass through the sample; and producing an output signal representative of the relative movement of the two light beams, said signal being proportional to the refractive index gradients present in the sample.

17. A method of detecting refractive index gradients according to claim 16, wherein the steps of producing an output signal representative of the relative movement of the two light beams include the steps of providing a photosensor having a sensing area and well defined edges of the sensing area in the direction perpendicular to the direction of flow through the sample chamber; aligning the photosensor and the light beams so that with no refractive index present in the sample through which the light beams pass, only complementary portions of each beam fall onto the sensing area of the photosensor whereby parallel movement of the beams will change equally the respective complementary portions sensed to maintain a constant output for the sensor, but movement of one beam relative to the other will produce a change in the output of the sensor proportional to the relative movement.

18. A detector for detecting refractive index gradients within a flowing sample along a gradient direction perpendicular to the direction of flow of the sample and providing an output proportional to the refractive index gradient detected, comprising an elongate sample chamber having side walls defining the sample chamber and having a sample chamber central axis and through which a sample flow in the direction of the central axis; a sensor having a sensing surface extending in a direction perpendicular to the direction of flow of the sample across the sample chamber central axis, said sensing surface having opposite end edges extending substantially parallel to the central axis and positioned intermediate the central axis and side walls of the chamber; a source of light; means for directing the light through the sample so that a portion of the light falls on the sensing surface of the sensor, a portion of the light falls off the sensing surface of the sensor at one of said opposite end edges of the sensing surface, and a portion of the light falls off the sensing surface of the sensor at the other of said opposite end edges of the sensing surface, and wherein the portions of the light falling off the sensing surface of the sensor at opposite end edges thereof are complementary portions so that movement of the light not caused by presence of a refractive index gradient in the path of the light will move the respective complementary portions of the light equally in the same direction so that the same amount of light falls on the sensing surface of the sensor to maintain a constant output from the sensor, but movement of the complementing portions with respect to one another as caused by a refractive index gradient in the path of the light will produce an output proportional to the relative movement.

* * * * *